(12) United States Patent
Cravens

(10) Patent No.: US 8,801,977 B2
(45) Date of Patent: *Aug. 12, 2014

(54) ENHANCED ALPHA PARTICLE EMITTER

(75) Inventor: Dennis Cravens, Cloudcroft, NM (US)

(73) Assignee: Brown-Cravens-Taylor, Sebastopol, CA (US)

( * ) Notice: Subject to any disclaimer, the term of this patent is extended or adjusted under 35 U.S.C. 154(b) by 265 days.

This patent is subject to a terminal disclaimer.

(21) Appl. No.: 13/587,506

(22) Filed: Aug. 16, 2012

(65) Prior Publication Data

US 2014/0191169 A1    Jul. 10, 2014

Related U.S. Application Data

(63) Continuation of application No. 12/967,730, filed on Dec. 14, 2010, now Pat. No. 8,303,865.

(60) Provisional application No. 61/286,711, filed on Dec. 15, 2009.

(51) Int. Cl.
*C09K 11/04* (2006.01)
*C09K 3/00* (2006.01)
*G21F 5/00* (2006.01)

(52) U.S. Cl.
USPC ............... 252/625; 250/506.1; 250/507.1; 252/478; 977/904

(58) Field of Classification Search
USPC ............... 250/506.1, 507.1; 252/478, 625; 977/904
See application file for complete search history.

(56) References Cited

U.S. PATENT DOCUMENTS

| | | | | |
|---|---|---|---|---|
| 5,098,645 | A * | 3/1992 | Forsberg | 376/272 |
| 8,303,865 | B1 * | 11/2012 | Cravens | 252/625 |
| 2007/0102672 | A1 * | 5/2007 | Hamilton | 252/478 |
| 2009/0186060 | A1 * | 7/2009 | Hainfeld et al. | 424/422 |

OTHER PUBLICATIONS

Cravens, Dennis, "Factors Affecting the Success Rate of Heat Generations in CF Cells", Fourth International Conference on Cold Fusion, 1993.
Cravens, D. et al., "Practical Techniques in CF Research" PowerPoint slides, Tenth International Conference on Cold Fusion, 2003.
Cravens, D. et al., "Practical Techniques in CF Research—Triggering Methods", Tenth International Conference on Cold Fusion, 2003.
Cravens, D. et al., "The Enabling Criteria of Electrochemical Heat: Beyond Reasonable Doubt", International Conference on Condensed Matter Nuclear Science, 2008.

* cited by examiner

*Primary Examiner* — Bijan Ahvazi
(74) *Attorney, Agent, or Firm* — Fish & Tsang, LLP

(57) ABSTRACT

A composition of matter that experiences an increase rate of radioactive emission is presented. The composition comprises a radioactive material and particles having affinity for Hydrogen or its isotopes. When exposed to Hydrogen, the composition's emission rate increases. Methods of production are also presented.

16 Claims, 2 Drawing Sheets

//]:# US 8,801,977 B2

ENHANCED ALPHA PARTICLE EMITTER

This application is a continuation of U.S. patent application having Ser. No. 12/967,730 filed Dec. 14, 2010 which claims the benefit of priority to U.S. provisional application having Ser. No. 61/286,711 filed Dec. 15, 2009. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is radioactive emission controlling technologies.

BACKGROUND

Many radioactive compositions of matter are known. Each composition of matter has a characteristic rate of emission with respect to its half-life. Interestingly, the emission rate can only be decreased via shielding or by the passage of time. More useful compositions would have a property that could increase their emissions rates in a controllable fashion without the use of shielding.

Pioneering effort has been put forth by the Applicant toward identifying such compounds. The following works describe the Applicant's previous efforts directed to identifying desirable compounds and were made available in the provisional application to which the instant application claims priority:

a. "Factors Affecting Success Rate of Heat Generation in CF Cells.", by Cravens, in Fourth International Conference on Cold Fusion. 1993. Lahaina, Maui: Electric Power Research Institute 3412 Hillview Ave., Palo Alto, Calif. 94304.

b. "Practical Techniques In CF Research—Triggering Methods" by Cravens et al., PowerPoint slides in Tenth International Conference on Cold Fusion. 2003. Cambridge, Mass.: see LENR-CANR.org.

c. "Practical Techniques In CF Research—Triggering Methods", by Cravens et al., in Tenth International Conference on Cold Fusion. 2003. Cambridge, Mass.: LENR-CANR.org. This paper was presented at the 10th International Conference on Cold Fusion. It may be different from the version published by World Scientific, Inc (2003) in the official Proceedings of the conference.

d. "The Enabling Criteria Of Electrochemical Heat: Beyond Reasonable Doubt", by Cravens et al. in ICCF-14 International Conference on Condensed Matter Nuclear Science. 2008. Washington, D.C.

What has yet to be appreciated is that a composition of matter can be made based on an a priori radioactive material, where the composition, when properly formulated, experiences an increased the radioactive emission rate under proper conditions. Such compositions of matter have value across many fields include semiconductor development, medicine, energy production, or other areas where greater control over radioactive emission would be beneficial.

Thus, there is still a need for compositions that have controllable emissions rates.

SUMMARY OF THE INVENTION

The inventive subject matter includes a composition of matter and methods of producing a composition of matter, where the composition has an adjustable emission rate. In one aspect of the inventive subject matter, a composition comprises metallic ions and a radioactive material disposed in a ceramic matrix. The composition has a first natural emission rate when unexposed to Hydrogen. When the composition is exposed to a hydrogen isotope, preferably in gaseous form, the composition's emission rate increases.

Various objects, features, aspects and advantages of the inventive subject matter will become more apparent from the following detailed description of preferred embodiments, along with the accompanying drawing figures in which like numerals represent like components.

DETAILED DESCRIPTION

One should appreciate that the disclosed techniques provide many advantageous technical effects including forming a composition of matter with a controllable emission rate.

Figure 1:
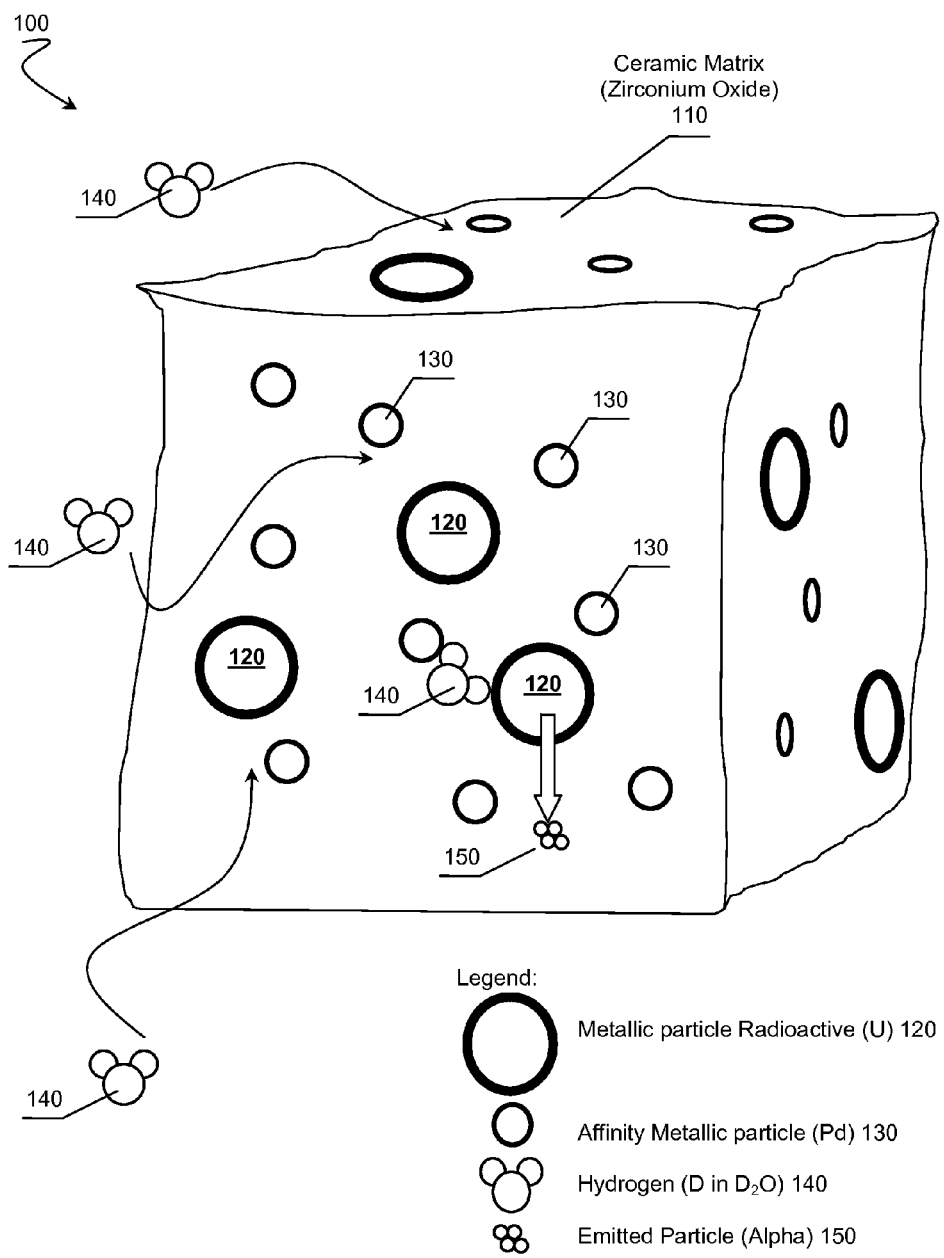
FIG. 1 is a representation of a composition of matter comprising radioactive materials bound in a ceramic matrix and having an adjustable emission rate.

In FIG. 1 composition of matter 100 comprises ceramic matrix 110, Zirconium Oxide for example, having bound metallic particles 120 and 130 where the metallic particles can include ionic versions of their elements. Radioactive metallic particles 120 represent a radioactive material having a characteristic half life. In the example shown, radioactive metallic particles 120 can include Uranium (U). Depending on the isotope of Uranium, Uranium's half-life can range from 68.9 years (U-232) to $4.4 \times 10^9$ years (U-238). The emission rate of composition 100 depends on the half life of radioactive metallic particles 120 and the amount of radioactive metallic particles 120 within composition 100. Affinity metallic particles 130 preferably comprise particles, or ions, that have an affinity for isotopes of Hydrogen (H), especially Deuterium (D), or even Tritium (T). As shown, affinity metallic particles 130 can include Palladium (Pd), which has been shown to have an affinity for Deuterium.

When composition 100 is bathed in a Deuterium containing fluid (e.g., gas, heavy water, etc.), affinity metallic particles 130 aid in causing ceramic matrix 110 to absorb Deuterium 140. Due to the presence of Deuterium 140, as confined by ceramic matrix 110, and in the presence of radioactive metallic particles 120, composition 100 experiences an increased rate of emission. In the example shown, composition 100 emits alpha particles 150 at an increased rate.

The following disclosure describes in more detail methods by which composition 100 can be formed. Although the preceding discussion has been presented in terms of Deuterium, one should appreciate that composition 100 has an affinity for Hydrogen in its various isotopes. Through absorption of Hydrogen, the radioactive signature of composition 100 can be modified.

Composition

Composition 100 can include between 5% and 35% by mass of Palladium by weight. Palladium increases absorption rates of Hydrogen or its various isotopic forms.

Composition 100 can also include between 5% and 35% by mass of Nickel (Ni) by weight in place of Palladium or in combination with Palladium.

Composition 100 can also include between 0.5% and 5% by mass of one or more of the elements with Z's from 57 to 71 (e.g., Lanthanum to Lutetium) inclusively.

Composition 100 can be configured so that the metallic grains of affinity metallic particles 130 are nominally below 1 micron and preferably isolated from each other within ceramic matrix 110. In some embodiments, grain sizes can range from 3 nm to 12 nm.

As stated above composition 100 can utilize Zirconium Oxide ceramic as ceramic matrix 110 which can also can contain and isolate the metallic particles 120 or 130.

Composition 100 can also utilize zeolites in place of zirconium oxide to contain and isolate the radioactive metallic particles 120 or affinity metallic particles 130.

Production

Figure 2:
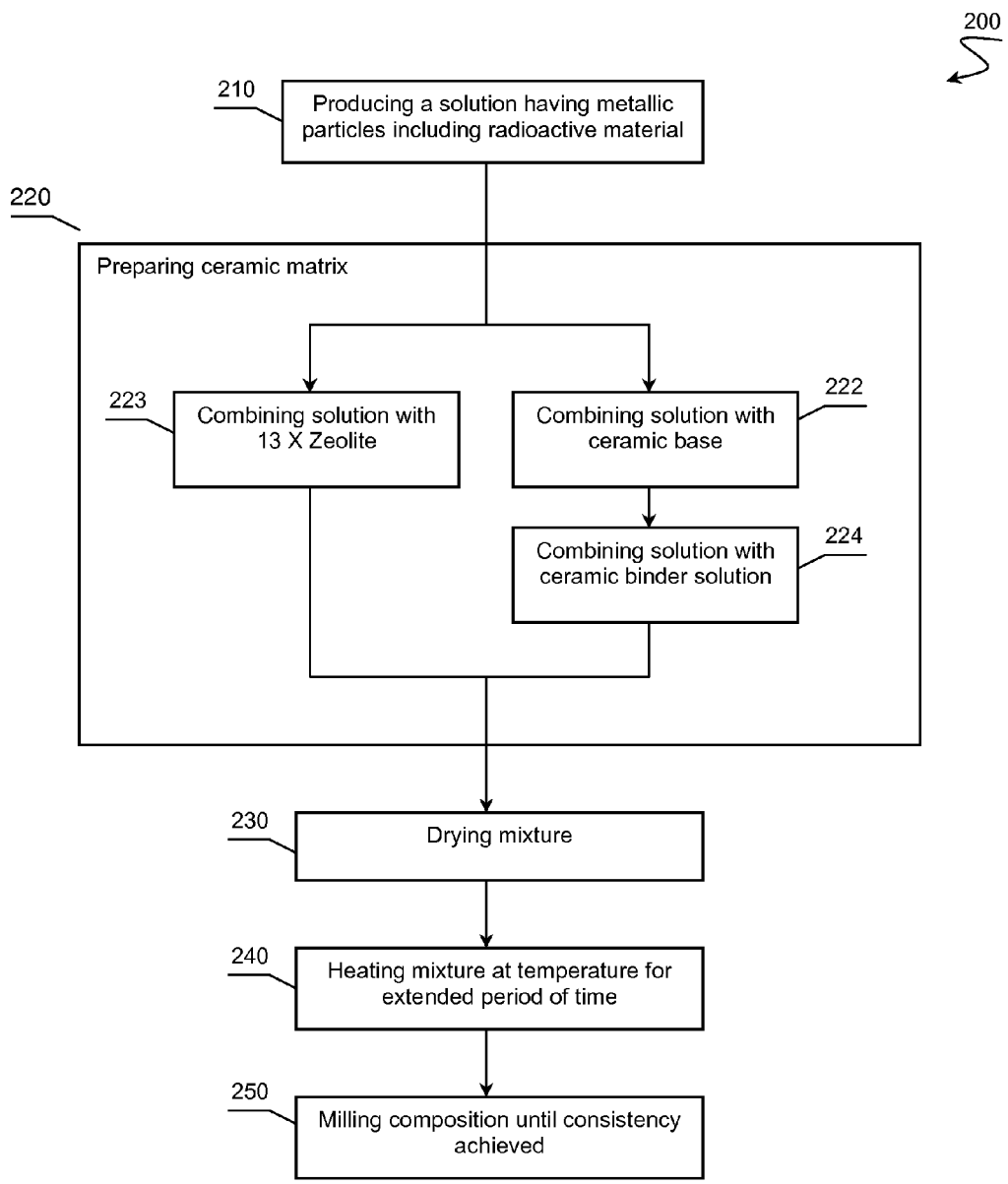
FIG. 2 is an example method for producing a composition matter having radioactive materials with an adjustable emission rate.

FIG. 2 presents method 200 by which one can produce compositions having radioactive signatures that can be modified in the presence of Hydrogen isotopes.

Step 210 includes producing a solution having metallic ions including radioactive material. For example, the following ingredients can be combined to form an acceptable solution:

a. 2 grams of Palladium Chloride
  b. 2.5 grams of Nickel Nitrate
  c. 2 grams of Strontium (Sr) Nitrate
  d. 1.3 grams of Uranium Acetate
  e. 2 grams of fine mischmetal
  f. 20 ml of heavy water Step 220 includes preparing the ceramic matrix along with the solution from step 210. The ceramic matrix can be combined with the solution at via at least two optional approaches. In some embodiments, taking the left path within step 220, step 223 can optionally include combining the solution from step 210 with 13× zeolite. To continue with the preceding example recipe, 55 grams of 13× zeolite would be sufficient. Combining the solution with the 13× zeolite can include placing the combined ingredients in a flask and mixing via a magnetic stirrer for about 48 hours at a temperature of about 70 degrees Celsius.

Alternatively, at step 222 the solution can be combined with a ceramic base, possibly including Zirconium Oxide. A preferred Zirconium Oxide includes 45 grams of Yttrium (Y) stabilized Zirconium Oxide. The solution and Zirconium Oxide can be further combined with a ceramic binder solution at step 224. An acceptable amount of the Zirconium Oxide binder solution is about 15 ml.

Regardless of the path choose for establishing the ceramic matrix, step 230 includes drying the mixture. For the amounts specified above, an acceptable drying time is about 24 hours while holding a temperature of 200 degrees Celsius while also holding the composition at a near vacuum (e.g., less than about 4 torr).

Once drying is complete, at step 250, the composition can be milled until it has a desired consistency. Typically, about 24 hours of ball milling is required to achieve a desired consistency.

Although a very specific recipe is presented, one should appreciate that the recipe can be varied to create larger or smaller batches of the novel composition. Therefore, the times, measures, or other values in the above production processes above can be varied while still falling within the scope of the inventive subject matter.

Material Sources

Materials used for making the novel composition can be obtained from commercial sources. For example, the following materials can be obtained from the referenced sources:

Zirconium Oxide ceramic and binder #760 from Cotronics, Corp.
  13× zeolite from Part #: 1212024 from Compressed Air
  Palladium Chloride, Reagent, ACS from Lab Depot
  Other chemicals from United Nuclear Experimental Results An experimental batch of the composition was prepared according to the above processes and its radioactive signature was measured. The finished composition was placed within a near vacuum of 4 torr at 100 Celsius for 8 hours to ensure the composition has sufficiently degassed. The composition was monitored for radiation using a Tennelec alpha counter and an Oxford detector. A count rate of 1364 counts per hour was observed. The composition was then allowed to absorb Deuterium gas at atmospheric pressure and again the radiation count rate was observed. Upon absorption of Deuterium the count rate increased to 3251 counts per hour. The increased emission rate was observed even though the rate should have decreased due to shielding by the gas at a higher pressure.

Applications

The above observed effect has utility for controlling or promoting nuclear radiation emission, or as a pressure monitor in deuterium gas systems.

An alpha emitter, possibly based on the above disclosed composition, which has a detectable change in emission rates in the presence of Deuterium gas could be used as a Deuterium gas sensor.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A radioactive composition of matter, comprising:
   a plurality of radioactive particles and a plurality of affinity metallic particles disposed in a ceramic matrix;
   wherein the plurality of affinity metallic particles have an affinity for isotopes of hydrogen;
   wherein the composition yields a first rate of emission and has an affinity to absorb an isotope of hydrogen; and
   wherein the composition yields a second, increased rate of emission in response to absorbing the isotope of hydrogen.

2. The composition of matter of claim 1, wherein the ceramic matrix comprises a zirconium oxide.

3. The composition of matter of claim 1, wherein the composition is configured to absorb the isotope of hydrogen in gaseous form.

4. The composition of matter of claim 1, wherein the radioactive particles comprises a Uranium salt.

5. The composition of matter of claim 4, wherein the Uranium salt comprises Uranium acetate.

6. The composition of matter of claim 1, wherein the affinity metallic particles include Palladium.

7. The composition of matter of claim 6, wherein the Palladium comprises between 5% and 35% by mass of the composition.

8. The composition of matter of claim 1, wherein the affinity metallic particles include Nickel.

9. The composition of matter of claim 8, wherein the Nickel comprises between 5% and 35% by mass of the composition.

10. The composition of matter of claim 1, further comprising 0.5% and 5% by mass of one or more elements having Z from 57 to 71.

11. The composition of matter of claim 1, wherein the affinity metallic particles comprise a plurality of grains having an average grain size of less than 1 micron.

12. The composition of matter of claim 11, wherein the grains are substantially isolated from each other.

13. The composition of matter of claim 12, further comprising zeolites that contain and isolate the grains.

14. The composition of matter of claim 11, wherein the ceramic matrix comprises zirconium oxide that contains and isolates the grains.

15. The composition of matter of claim 1, wherein the isotope of hydrogen comprises Deuterium.

16. The composition of matter of claim 1, wherein the isotope of hydrogen comprises Tritium.

* * * * *